United States Patent [19]

Shirota

[11] Patent Number: 5,368,572
[45] Date of Patent: Nov. 29, 1994

[54] INJECTION DEVICE FOR DENTAL ANESTHETIC OR LIKE

[75] Inventor: Kazunari Shirota, Tokyo, Japan

[73] Assignee: Shirota Denki Rozai Kabushiki Kaisha, Tokyo, Japan

[21] Appl. No.: 113,672

[22] Filed: Aug. 31, 1993

[30] Foreign Application Priority Data

Jan. 6, 1993 [JP] Japan .................. 5-2567

[51] Int. Cl.5 ............................. A61M 5/24
[52] U.S. Cl. ........................ 604/154; 604/155
[58] Field of Search ............ 604/155, 413, 154, 152

[56] References Cited

U.S. PATENT DOCUMENTS

| | | | |
|---|---|---|---|
| 3,456,649 | 7/1969 | Jewett | 604/155 |
| 3,631,847 | 1/1972 | Hobbs, II | 604/155 |
| 3,701,345 | 10/1972 | Heilman et al. | 604/155 |
| 3,701,350 | 10/1972 | Guenther et al. | 604/155 |
| 3,720,211 | 3/1973 | Kyrias | 604/155 |
| 3,812,843 | 5/1974 | Wootten et al. | 604/155 |
| 4,109,177 | 8/1978 | Astor | 604/155 |
| 5,033,476 | 7/1991 | Kasai | 604/413 |
| 5,122,327 | 5/1992 | Iinuma et al. | 604/413 |
| 5,244,461 | 9/1993 | Derlien | 604/155 |
| 5,269,762 | 12/1993 | Armbruster et al. | 604/155 |
| 8,034,003 | 7/1991 | Denance | 604/155 |

*Primary Examiner*—Paul J. Hirsch
*Attorney, Agent, or Firm*—Browdy and Neimark

[57] ABSTRACT

An injection device for a dental anesthetic or the like is constituted such that the linkage between the rear end side of an operating rod provided so as to freely go in and out of a main body and a drive mechanism operated by a motor provided in the main body is made detachably and the connecting or disconnecting operation of the drive mechanism and the rear end side of the operating rod is carried out by means of a manipulation portion provided in the main body.

1 Claim, 3 Drawing Sheets

FIG. 1 *(PRIOR ART)*
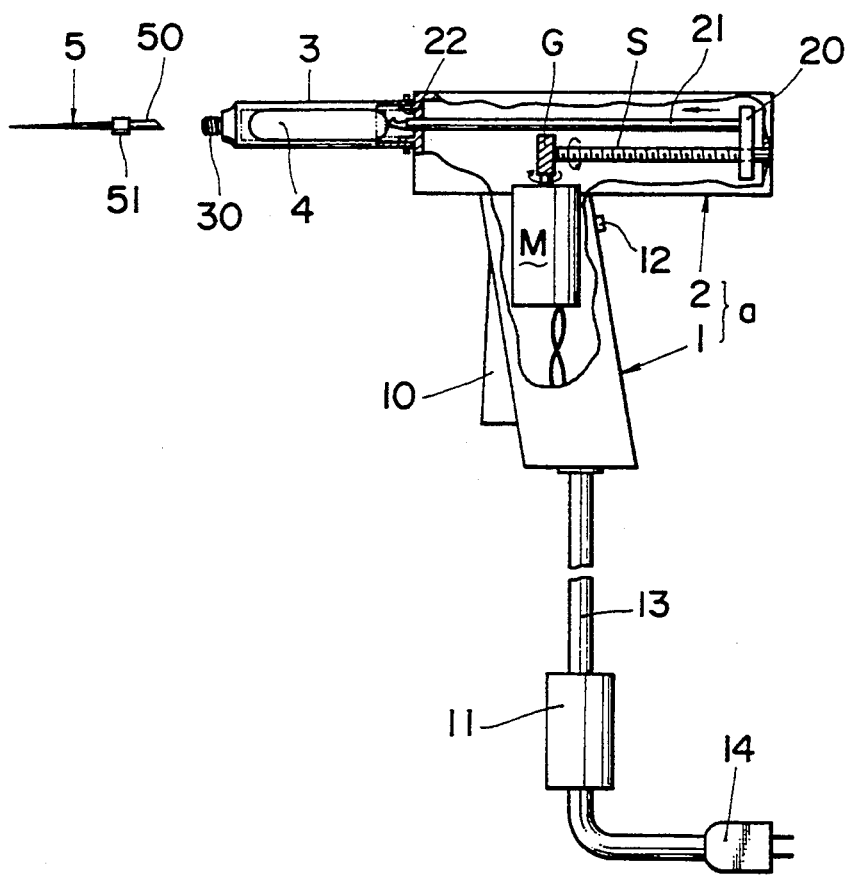
FIG. 2
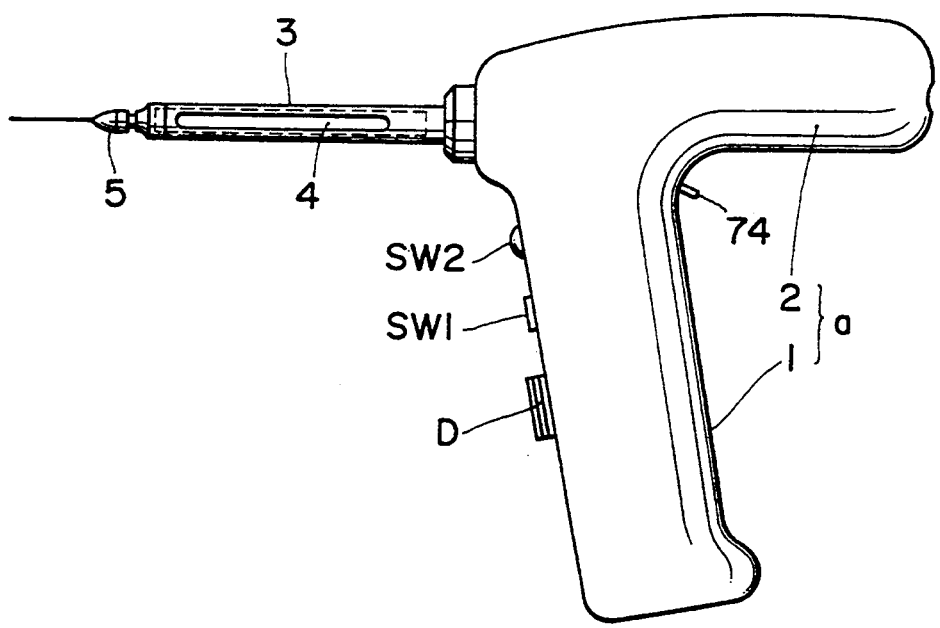

INJECTION DEVICE FOR DENTAL ANESTHETIC OR LIKE

BACKGROUND OF THE INVENTION

1. Field of the Invention

This invention relates to an improvement in an injection device for a dental anesthetic or the like utilized when a dentist injects an anesthetic into a patient's gingiva for the dental treatment of a patient in dental care.

2. Description of the Prior Art

A means disclosed in Japanese Utility Model Laid-open No. 53-43748 has been known with reference to an injection device for a dental anesthetic or the like.

With respect to this means, a main body a is formed by mounting integrally and continuously an operating portion case 2, which is formed in an axially cylindrical form having an axial direction set as a longitudinal direction thereof, on the upper end side a handle portion 1 having a size large enough to be grasped by a hand and formed in an axially cylindrical form having an axial direction set as a longitudinal direction thereof, as shown in FIG. 1. Then, a motor M is internally built in the handle portion 1 of the main body, and a switch lever 10 for controlling a drive circuit of the motor M to be on and off is mounted on the front side of the handle portion. In addition, the switch lever 10 is linked with a control circuit within a control box 11 separately provided so as to variably control the rotational speed of the motor M according to the depth in gripping the handle portion, and a switch 12 is provided on the rear side of the handle portion so as to reverse the rotational direction of the motor M.

In the operating portion case 2, a screw shaft S transmitted from and rotated by the output shaft of the motor M through a worm gear G is accommodated and axially suspended at such a posture that an axial direction thereof is set along the longitudinal direction, and a driver 20 provided so as to slide back and forth within the operating portion case 2 is screwed onto the screw shaft S so that the driver 20 is moved back and forth by the rotation of the screw shaft S. The rear end of an operating rod 21 having the rear end side projected into the operating portion case 2 at such a posture that a longitudinal direction thereof is set along the longitudinal direction is integrally connected to the driver 20 so that the front end side of the operating rod 21 is operated to go in and out of the front end of the operating portion case 2 by operating the motor M. Then, a connection hardware 22 for connecting a cartridge holder 3 to the operating portion case 2 is provided on the front end of the operating portion case in such a ring form as to surround the front end side of the operating rod 21 for making the going in-and-out operation described above, and the front end of the operating portion case is connected with the base end of the cartridge holder 3 loaded with a cartridge 4, in which an injection is sealed. An injection needle 5 having a communicating needle 50 provided on the base end side so as to be projected into the sealed portion of the front end of the cartridge 4 is mounted on an injection needle connection hardware 30 provided on the tip end side of the cartridge holder 3. The injection device of the prior art is constituted so as to inject an injection by operating the switch lever 10 to operate the motor M under the condition that a plug socket 14 at the tip end of a power source cord 13 drawn to the lower end side of the handle portion 1 is plugged in the socket of a commercial power source.

The means described above enables injection of an anesthetic into a patient's gingiva at such an extremely slow speed as to give no pain to the patient by controlling the depth in gripping the switch lever 10 when the anesthetic is injected into the patient's gingiva. However, in case of exchanging the injection needle 5 and the cartridge 4 with a new injection needle 5 and a new cartridge 4 for every patient for the prevention of an infectious disease, it is necessary to return the operating rod 21 in such a projected condition thereof to push a piston 41, which is made of a rubber plug on the rear end side of the cartridge 4, into the cartridge 4 in the operation when a drug is injected into the previous patient, to the condition that the operating rod is drawn in by reversely rotating the motor M by the operation of the reverse rotation switch 12. Since the operation for the process described above is slow and it requires a long waiting time, this prior art has a disadvantage in that the prompt exchange of the injection needle with a new one is not possible.

Since the operation for drawing back the operating rod 21 by operating the switch 12 is assumed as an object for the case that the aspiration operation is carried out for confirming the condition that the needle 5 is pierced into a predetermined portion of the patient's gingiva up to a predetermined depth when the needle 5 is pierced into each patient's gingiva, the speed for the operation of the operating rod 21 is set to be extremely slow.

Since the injection of an anesthetic by pushing out the operating rod 21 is set up in an extremely slow speed to such an extent that no pain is given to each patient, the variable control of the rotational speed of the motor M by the control of the depth in gripping the switch lever 10 cannot also accelerate the drawing-back speed of the operating rod 21, even though this control circuit is used. Furthermore, even though the rotation of the motor M is switched over to a high speed rotation by use of decelerating means composed of the worm gear G for the transmission between the screw shaft S and the output shaft of the motor M, the prior art takes such an impossible mechanism as to move the operating rod at high speed.

SUMMARY OF THE INVENTION

It is accordingly a primary object of the present invention to provide new means, which can control the protruding speed of an operating rod in a slow speed such that the injection of an anesthetic gives no pain to a patient, and can promptly carry out the drawing-back operation of the operating rod for exchanging the cartridge with a new one, while the aspiration operation (drawing-back operation) for confirming whether or not the piercing of a needle is made in a predetermined condition is carried out to be controlled in a slow speed.

According to the present invention, in an injection device for a dental anesthetic or the like, in which the rear end side of an operating rod is accommodated in a main body composed of a handle portion in an axially cylindrical form and an operating portion case connected to the upper portion of the handle portion so that the front end side of the operating rod is operated to go in and out toward the cavity of a cartridge holder detachably connected to the front end portion of the operating portion case, a drive mechanism operated by a motor built in the main body is linked to the rear end side of the operating rod, both a drive switch for controlling the motor so as to normally rotate and a reverse switch for controlling the motor so as to reversely rotate are provided on the outside face of the main body, an injection needle having a communicating needle pierced into a membrane at the front end of a cartridge accommodated in the cartridge holder on the base end side is detachably connected to the front end of the cartridge holder, and a hook portion engaged with a piston made of a rubber material and provided on the rear end side of the cartridge is provided on the front end of the operating rod, the improvement comprises a manipulation portion provided on the outside face of the main body, wherein the drive mechanism is linked to the rear end side of the operating rod detachably, and the manipulation portion allows the drive mechanism and the rear end side of the operating rod to carry out the connecting or disconnecting operation of the linkage.

BRIEF DESCRIPTION OF THE DRAWINGS

The foregoing and other objects and features of the invention will become apparent from the following description of a preferred embodiment of the invention with reference to the accompanying drawings, in which:

FIG. 1 is a side view, partly broken-away, showing an injection device for a dental anesthetic or the like of the prior art;

FIG. 2 is a side view showing an injection device for an anesthetic or the like as a preferred embodiment of the present invention;

DETAILED DESCRIPTION OF THE PREFERRED EMBODIMENT

Figure 3:
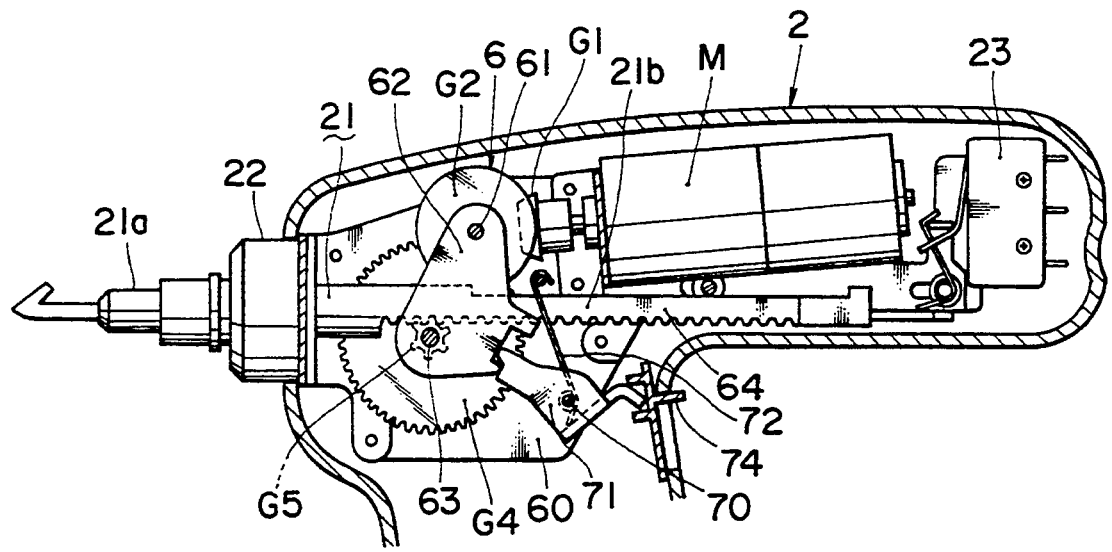
FIG. 3 is a longitudinal cross-sectional view showing the main portion of FIG. 2.

FIG. 2 is a side view showing an injection device for a dental anesthetic or the like as a preferred embodiment of the present invention. In the drawing, a indicates a main body, 1 indicates a handle portion, 2 indicates an operating portion case, 3 indicates a cartridge holder for connecting the base end side to a connection hardware 22 at the front end of the operating portion case 2, 4 indicates a cartridge accommodated in the cartridge holder 3 so as to be loaded, and 5 indicates an injection needle connected and attached to the front end of the cartridge holder 3, respectively.

The main body a comprises the handle portion 1 formed in an axially cylindrical form so as to have a size large enough to be grasped by a hand and the operating portion case 2 connected to one end side of the handle portion 1 in such a posture that an axial direction thereof is orthogonal to the handle portion.

A storage battery chargeable by connecting the storage battery to a commercial power source is accommodated in the internal hollow portion of the handle portion 1. An attachment plug of a cord connected to the socket of the commercial power source can be inserted into a jack provided at the bottom of the handle portion to permit charging of the battery.

A drive switch SW1 operates to switch on a drive circuit of a motor M accommodated in the operating portion case 2 as shown in FIG. 3 and for normally rotating the motor M and a reverse rotation switch SW2 for reversely rotating the motor M by operating to switch on the drive rotation are mounted on the outside face of the handle portion 1. Furthermore, a control dial D for adjusting the rotational speed of the motor M under the condition that the drive switch SW1 is switched on is provided on the outside face of the handle portion.

As shown in FIG. 3, the motor M operated by the storage battery, a control portion 23 provided with a control circuit for controlling the operation of the motor M, a rear end side 21b of the operating rod 21 having a front end side 21a operated going in and out of the connection hardware 22 at the front end of the operating portion case 2, and a drive mechanism 6 for driving the operating rod 21 so as to cause the operating rod to operate going in and out by transmitting to the output shaft of the motor M are incorporated into the internal portion of the operating portion case 2, respectively.

Figure 4:
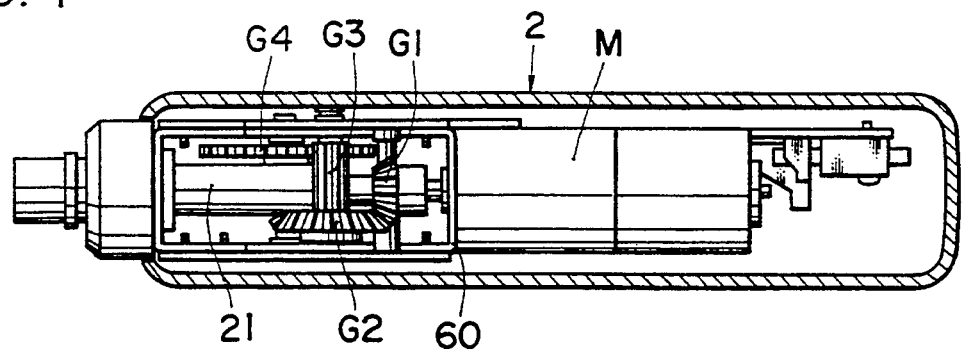
FIG. 4 is a cross-sectional plan view showing the main portion of FIG. 2.
Figure 5:
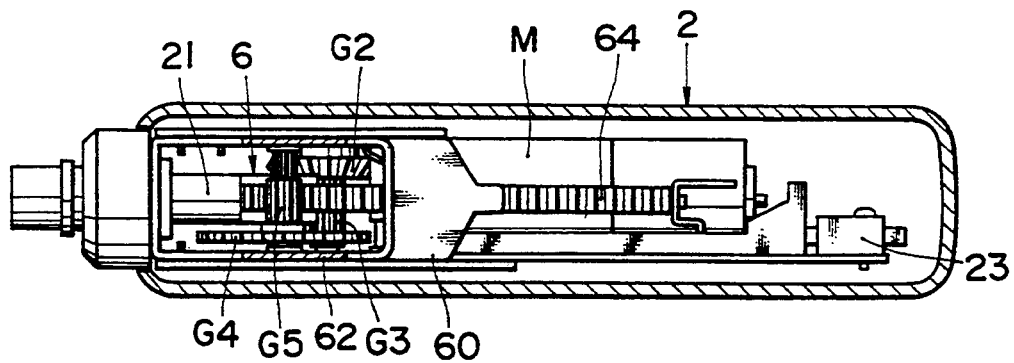
FIG. 5 is a cross-sectional bottom view showing the main portion of FIG. 2.

As shown in FIGS. 3 through 5, the drive mechanism 6 comprises a bevel gear G1 installed to the output shaft of the motor M, another bevel gear G2 rotated while being engaged with the bevel gear G1 and axially supported by a support shaft 61 to a frame 60 assembled in the operating portion case 2, a small-diameter gear G3 integrally rotated with the bevel gear G2 while being freely and axially supported by the support shaft 61 of the bevel gear G2, a large-diameter gear G4 rotated while being engaged with the small-diameter gear G3 by axially supporting a rotation axis 63 by a pivotal frame 62 pivotally moved around the support shaft 61, a drive pinion G5 integrally rotated with the rotation axis 63 while being fit to the rotation axis 63 of the large-diameter gear G4, and a rack 64 engaged with the drive pinion G5 and provided on the rear half side of the operating rod 21.

Figure 6:
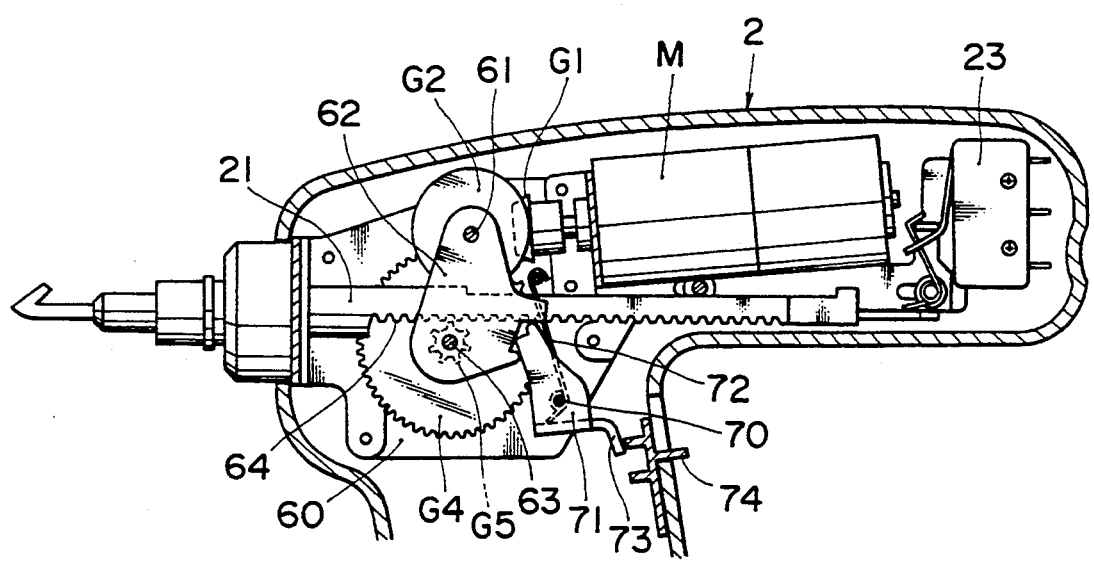
FIG. 6 is a longitudinal cross-sectional side view showing the condition that the linkage between an operating rod and a drive mechanism is released by a manipulation member in the main portion of FIG. 2.
Figure 7:
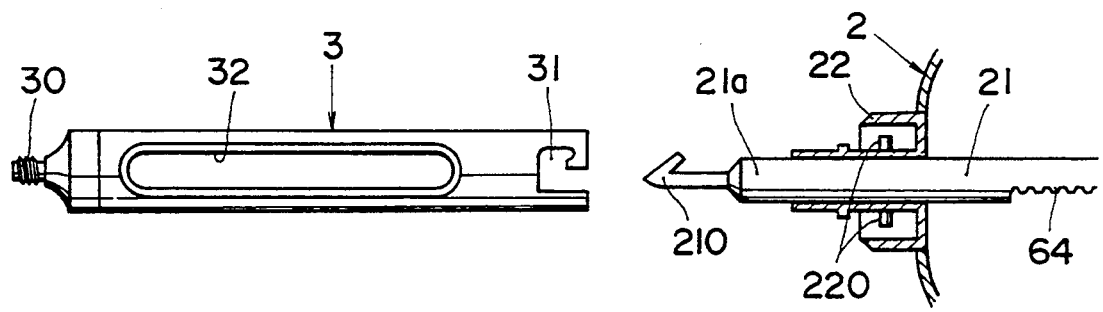
FIG. 7 is a side view, partly broken-away, showing a cartridge holder and a front end portion of an operating portion case in FIG. 2.

With reference to this drive mechanism 6, the drive pinion G5 axially supported to the pivotal frame 62 is kept in the condition to be apart downward from the rack 64, intercept the transmission to the operating rod 21 and to operate the operating rod 21 so as to freely go in and out independently of the drive mechanism 6 as shown in FIG. 6, since the pivotal frame 62 for axially supporting the drive pinion G5 is pivoted counterclockwise in FIG. 3 around the support shaft 61 of the bevel gear G2.

Also, since the pivotal frame 62 for axially supporting the drive pinion G5 is biased to pivot counterclockwise around the support shaft 61 in FIG. 3 by a spring pressure for biasing the pivotal arm 71, which is axially supported to the frame 60 so as to freely pivot around the support shaft 70, counter-clockwise around the support shaft 70 in FIG. 3 by means of a torsion spring 72, the drive pinion G5 brought into such a condition that the transmission between the drive mechanism 6 and the operating rod 21 is intercepted is kept to occupy a position where the drive pinion G5 is engaged with the rack 64 as shown in FIG. 3. On the other hand, when the pivotal arm 71 is pivoted clockwise around the support shaft 70 in FIG. 3 against the biasing due to the torsion spring 72 and the pivotal frame 62 linked to the pivotal arm 71 is pivoted clockwise around the support shaft 61 as shown in FIG. 6, the drive pinion G5 is moved to a position where the drive pinion G5 and the rack 64 come to be out of engagement.

Furthermore, the operation for allowing the pivotal arm 71 to pivot against the biasing due to the torsion spring 72 is ready to be carried out at any times by operating a manipulation portion 74, since the manipulation portion 74 freely sliding upward or downward is provided at an upper portion of the rear face side of the handle portion 1 and the manipulation portion 74 is linked to the operating arm 73 installed to the pivotal arm 71.

The cartridge holder 3 attached to the connection hardware 22 provided at the front end of the operating portion case 2 is a known cartridge holder which is formed in a sheath shape in which an angle-shaped engagement channel 31 engaged with engagement pins 220 provided in the connection hardware 22 is provided on the base end side, an observation port 32 is provided on the side of a peripheral wall of a barrel and an injection needle connection hardware 30 for the injection needle 5 is screwed in and attached to the tip end thereof. The cartridge holder 3 is normally attached by inserting the base end side of the cartridge holder into the connection hardware 22 under the condition that the engagement channel 31 installed at the base end side faces to the engagement pins 220 of the connection hardware 22 and by engaging the engagement channel 31 with the engagement pins 220 while rotating the cartridge holder from this condition.

Figure 8:
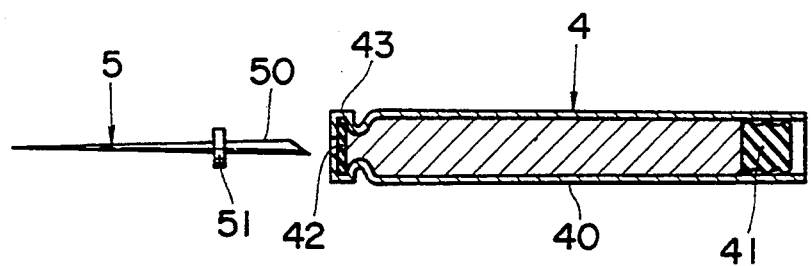
FIG. 8 is a side view, partly broken-away, showing a cartridge and an injection needle of FIG. 2.

As shown in FIG. 8, the cartridge 4 is a normal one constituted by loading anesthetics or the like in a transparent glass cylinder 40, inserting a piston 41 made of a rubber material in the base end side, installing a membrane 42 of the rubber material with a caulking hardware 43 to seal the membrane on the tip end side. The cartridge 4 is also in such a form that it is loaded in the cartridge holder 3 and used by mounting the cartridge holder 3.

The injection needle 5 is such a normal one as having a connection screw portion 51 provided on the base end side and screwed with an injection needle connection hardware 30 mounted on the tip end portion of the cartridge holder 3 and also having a communicating needle 50 provided on the rear face side of the connection screw portion 51 and pierced into the membrane 42 of the front end of the cartridge 4.

Furthermore, a hook portion 210 is provided on the front end of the operating rod 21 operated to go in and out of the axial core portion of the connection hardware 22 at the front end of the operating portion case 2 in order to allow the rubber-made piston 41 of the cartridge 4 to be drawn back for doing aspiration operation when the drawing-back operation is done under the condition that the operating rod 21 is pierced into the piston 41 and engaged with the piston 41.

The overall operation is as follows. The cartridge holder 3 accommodating the cartridge 4 therein is connected to the connection hardware 22 at the front end of the operating portion case 2, and the injection needle 5 is mounted on the front end of the cartridge holder 3 to give a condition of FIG. 2. When the handle portion 1 gripped and the drive circuit for the motor M is switched on by operating the drive switch SW1, the operating rod 21 is pushed out through the drive mechanism 6 and the piston 41 of the cartridge 4 is thereby pushed in. As a result, a drug such as anesthetics in the cartridge 4 is injected from the injection needle 5.

The rotational speed of the motor M for pushing out the operating rod 21 at this time is controlled to a desirable speed by the rotational position of a dial D. Therefore, the resulting injection speed of the drug from the injection needle 5 is controlled to such an extremely small quantity as desirably determined.

If the drive switch is released and the reverse rotation switch SW2 is switched on, the motor M is reversely rotated to draw in the operating rod 21 and the resulting aspiration operation comes to be done. This aspiration operation can be done at the speed which is applicable to the aspiration of an extremely small quantity which is done when the injection needle 5 is pierced into a patient's gingiva.

Then, when an old cartridge 4 is replaced with a new one in order to manage a new patient, the cartridge holder 3 is removed to take out the cartridge 4 and the drive pinion G5 is moved to the position separated from the rack 64 mounted on the rear end side of the operating rod 21 by operating the manipulation portion 74. As a result, the operating rod 21 is brought into a freely movable condition. Therefore, the operating rod 21 is returned to the first position by pushing the operating rod into with hands. Accordingly, the operation for returning the operating rod 21 to the initial position so as to exchange the old cartridge with a new one can be done instantly.

As described above, according to the injection device for a dental anesthetic or the like of the present invention, the operating rod 21 allowed to operate going in and out of the cavity of the cartridge holder 3 is brought into a free condition with respect to the drive mechanism 6 and the output shaft of the motor M by the operation of the motor M controlled by the operation of the drive switch SW1 and the reverse rotation switch SW2 are mounted on the outside face of the main body a, since the operating rod 21 is disconnected from the drive mechanism 6 driven by the motor M by operating the manipulation portion 74 mounted on the outside face of the main body. Therefore, the necessarily practiced operation for returning the operating rod 21 to the utmost drawn-in position can come to be done instantly by removing the linkage of the operating rod 21 to the drive mechanism 6 by operating the manipulation portion 74 and by pushing the operating rod 21 into the cartridge holder 3, when the cartridge 4 loaded in the cartridge holder 3 is exchanged with a new cartridge 4 for each patient. Since the operation of the motor M by operating the reverse rotation switch SW2 causes the operating rod 21 to be drawn in the cartridge 4 at a controlled low speed, the resulting waiting time before the operation comes to an end becomes unnecessary, and it becomes possible to exchange the cartridge 4 with a new one promptly.

What is claimed is:

1. In an injection device for a dental anesthetic or the like, having a rear end side of an operating rod accommodated in a main body including a handle portion in an axially cylindrical form and an operating portion case connected to the upper portion of the handle portion to allow a front end side of said operating rod to go in and out toward a cavity of a cartridge holder detachably connected to a front end of said operating portion case, a drive mechanism operated by a motor contained in the main body linked to the operating rod, a drive switch for controlling the motor to allow said motor to normally rotate and a reverse rotation switch for controlling said motor so as to allow said motor to reversely rotate, said drive switch and said reverse rotation switch provided on the outside face said main body, an injection needle having a communicating needle provided at a base end side, said injection needle detachably connected to a front end of said cartridge holder, said communicating needle extending through a membrane at a front end of a cartridge when housed in said cartridge holder, and a hook portion on the front end of said operating rod abutting a piston in a rear end side of said cartridge, an improvement of said injection device comprising, manipulation means located between the drive mechanism and the operating rod for selectively engaging or disengaging the drive mechanism to and from the operating rod, said manipulation means including actuating means on an outside face of the main body for permitting an operator to selectively engage or disengage the drive mechanism to and from the operating rod, wherein when the drive mechanism and the operating rod are disengaged the operating rod can be manually moved to quickly accommodate replacement of a used cartridge.

* * * * *